United States Patent [19]

Meier et al.

[11] 4,423,720

[45] Jan. 3, 1984

[54] PATELLAR STABILIZING ORTHOSIS

[75] Inventors: Robert H. Meier; Evelyn Farr, both of Jackson, Mich.

[73] Assignee: Camp International, Inc., Jackson, Mich.

[21] Appl. No.: 378,503

[22] Filed: May 17, 1982

[51] Int. Cl.$^3$ ............................................... A61F 3/00
[52] U.S. Cl. .................................... 128/80 C; 128/165
[58] Field of Search ............... 128/80 C, 87 R, 165; 2/22, 24

[56] References Cited

U.S. PATENT DOCUMENTS

| | | | |
|---|---|---|---|
| 3,046,981 | 7/1962 | Biggs, Jr. et al. | 128/80 C |
| 3,387,305 | 6/1968 | Shafer | 2/22 |
| 3,804,084 | 4/1974 | Lehman | 128/80 C |
| 3,831,467 | 8/1974 | Moore | 128/80 C |
| 3,926,186 | 12/1975 | Nirschl | 128/165 |
| 3,945,046 | 3/1976 | Stromgren | 2/22 |
| 4,296,744 | 10/1981 | Palumbo | 128/80 C |

Primary Examiner—John D. Yasko
Attorney, Agent, or Firm—Beaman & Beaman

[57] ABSTRACT

The invention pertains to a patellar stabilizing orthosis used in conjunction with rehabilitation programs involving all nonsurgical patella dislocations or mal-alignments including chondromalacia patellae, dislocation of the patella or subluxation of the patella. The orthosis is designed to achieve left or right lateral or left or right medial stability, and includes a U-shaped body member formed of nonelastic material wherein parallel legs extend from a base portion. A pad located adjacent the inner surface of the base portion is positioned laterally with respect to the patella and the legs are wrapped about the wearer's thigh and calf, and fastened in an overlapped manner. A pair of elastic straps affixed to the body base portion extend obliquely therefrom in a direction opposite to that of the legs and are affixed to the legs while under tension to produce the desired traction against the patella. The use of a reinforcing stay at the base portion, the attaching of the elastic straps to the central region of the base portion adjacent the stay, and the configuration of the cushioned pad combine to concentrate the force imposed upon the patella to effectively apply the stabilizing forces without unduly restricting leg use.

8 Claims, 7 Drawing Figures

PATELLAR STABILIZING ORTHOSIS

BACKGROUND OF THE INVENTION

Persons engaged in physical activities often incur damage to the knees. Such damage often is due to the overstressing or stretching of knee ligaments, and injury also occurs to the cartilage and articular surfaces of the joint. Treatment of the subluxation of the patella often includes surgery, but surgery, particularly with children, is undesirable due to the fact that the ligaments are not fully developed and are relatively loose during development, and surgery should be deferred until growth of the ligaments and knee plates has been completed.

It has now been recognized that many knee problems can be significantly improved, and surgery may be permanently avoided, if the patella is stabilized during activity, and such stabilization may be lateral or medial depending upon the particular problem being encountered. While a number of prior art knee supporting braces and splints have been proposed, such devices prevent or severely limit normal knee flexion and movement, and conventional prior devices restrict normal use of the knee and leg and do not provide the necessary patellar bracing during normal leg use.

A dynamic patellar brace is disclosed in U.S. Pat. No. 4,296,744 which overcomes many of the problems of prior art braces with respect to the stabilizing of the patella, and is capable of achieving lateral and medial stability. In this patented brace an elastic sleeve surrounds the knee and a pad located upon the sleeve is positioned as desired with respect to the patella. A pair of elongated elastic arm members are attached to the pad and are wrapped in a first direction above and below the patella, respectively, and include fasteners for retaining the legs in a tension and binding condition. A counter arm having an end centrally attached to the pad extends away from the legs, and is wrapped about the knee and includes an outer end which fastens to one of the legs and further binds the knee and forces the pad against the patella. While this patented brace produces a stabilizing pressure upon the patella, the presence of the elastic sleeve, and the binding action resulting from the two elastic arms, and the elastic counter arm, can easily become excessive if special care and skill is not utilized when applying the brace, and the use of four elastic and highly binding components interferes with the flexing and normal use of the knee. Also, the use of a single counter arm produces a nonsymmetrical force on the brace and the use of the sleeve requires an inventory of sleeve sizes.

It is an object of the invention to provide a patellar stabilizing orthosis for treating patellar subluxation wherein undue restriction of movement at the knee does not occur, and the likelihood of excessive binding or circulation problems is minimized.

Another object of the invention is to provide a patellar stabilizing orthosis which eliminates posterior knee binding, eliminates undesired stress to the patellar and knee joint, and avoids compression over the patella, and allows an unrestricted range of motion.

Yet a further object of the invention is to provide a patellar stabilizing orthosis wherein the pressure applied to the patellar may be accurately controlled and is symmetrical to the patellar, will not become excessive, and yet sufficient stabilization of the patella is achieved to provide effective treatment, often avoiding surgery.

An additional object of the invention is to provide a patellar stabilizing orthosis which may be economically manufactured, is usable with a variety of sizes of limbs to reduce inventory, is readily placed upon the knee and adjusted for use, and may be worn under many other types of knee supports.

In the practice of the invention the patellar stabilizing orthosis includes a generally U-shaped body of a nonelastic fabric material. The outer surface of the body is preferably of a nylon fabric having tightly woven loops for cooperation with hooked fasteners of the type available under the trademark "Velcro". The body includes a base portion from which extend a pair of parallel legs having Velcro type hook fasteners affixed to their outer free ends. The inner surface of the body member, including the legs, is a cushioned foam to insure comfortable wear.

A reinforcing stay receiving pocket is transversely disposed across the base portion, and a pair of elastic straps are affixed to the central region of the pocket at the body outer surface and are obliquely disposed to the length of the legs. A cushioned foam pad is located upon the inner side of the base portion in opposite relationship to the reinforcing stay, and the pad is located within a fabric pouch for ease of removal during cleaning.

In use, the supporting pad is positioned laterally of the patella and the arms are wrapped about the thigh and calf, respectively, in a direction away from the pad. The length of the legs is sufficient to encompass the thigh and the calf, and the free ends of the legs are attached to the legs' outer surfaces upon encircling the wearer's leg. Thereupon, the elastic straps are tensioned as desired to force the cushioned pad against the patella. As the elastic straps extend over the pad, and as the reinforcing stay also extends over the pad, an effective compression of the pad upon the patella is achieved, and the free ends of the straps are provided with hooked Velcro fasteners for attachment to the outer surfaces of the adjacent body legs.

As the orthosis of the invention does not require an elastic knee sleeve, and as the body legs are nonelastic, overcompression of the leg in the region of the knee is not likely to occur, and the installer easily regulates the compression produced by the non-stretchable legs. As the legs are wrapped in a direction away from the patella, and as the elastic straps are disposed over the cushioned pad in a direction toward the patella, the stabilizing force produced by the pad is most effectively utilized without imposing restrictive binding forces upon the knee, and the orthosis permits full flexion of the knee during use. The ends of the elastic straps are obliquely oriented to the legs and pass above and below the patella and do not overlie the patella to produce a rearward compression, and as the elastic straps are symmetrically related to the patella an even lateral force is applied to the patella devoid of a vertical vector.

BRIEF DESCRIPTION OF THE DRAWINGS

The aforementioned objects and advantages of the invention will be appreciated from the following description and accompanying drawings wherein.

DESCRIPTION OF THE PREFERRED EMBODIMENT

Figure 1:
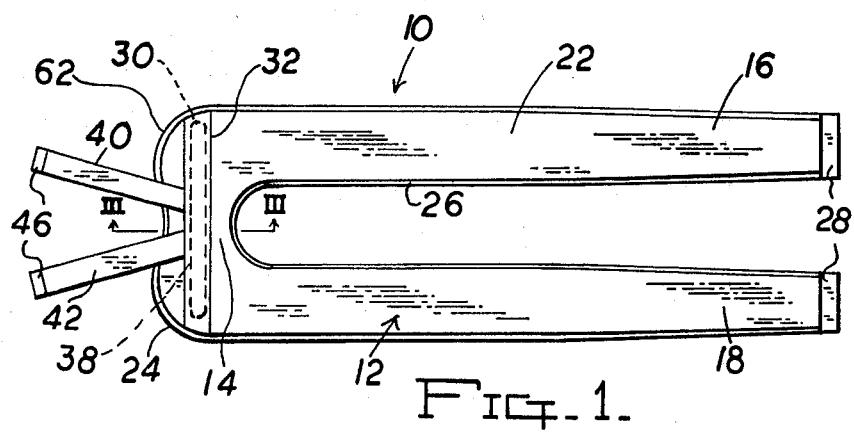
FIG. 1 is an elevational view of the patella stabilizing orthosis of the invention opened to a flat position with the outer surface disposed toward the viewer.
Figure 2:
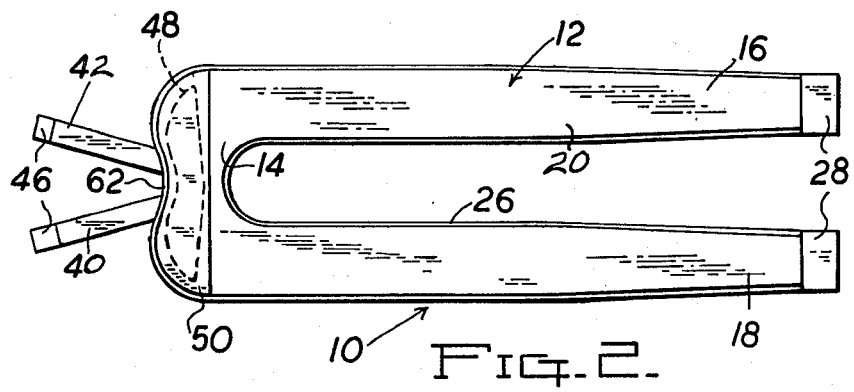
FIG. 2 is an elevational view of the orthosis similar to FIG. 1 with the inner surface disposed toward the viewer.
Figure 3:
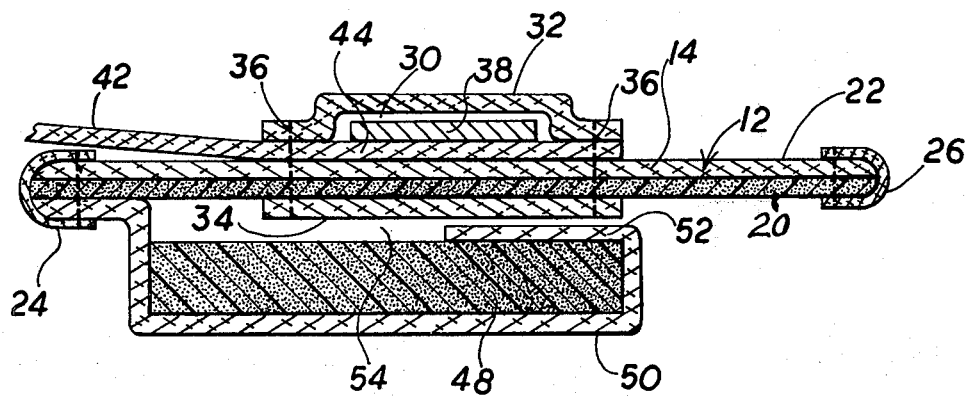
FIG. 3 is an elevational sectional view taken through the base portion and cushion pad along Section III—III of FIG. 1.

The construction of a patellar stabilizing orthosis in accord with the invention is best illustrated in FIGS. 1-3. The orthosis 10 includes a U-shaped body 12 having a base portion 14 from which extend substantially parallel legs 16 and 18 of equal length. The body 12 is formed of a nonelastic fabric, such as of nylon, and the outer surface 22 of the fabric is formed with a looped texture of the type commonly used with fasteners available under the "Velcro" trademark. The inner surface, FIG. 2, of the body is formed by a foam cushion 20 synthetic material disposed over the entire inner surface of the body 12, and the body 12 and cushion 20 are bound at their outer edges by a sewn binding 24 and at the inner edges of the legs by sewn binding 26.

The length of the legs 16 and 18 is such as to permit the legs to be wrapped about the lower thigh and upper calf of the user adjacent the knee, as later described, and a Velcro hook fastener patch 28 is sewn to the free end of each leg whereby upon the leg being wrapped about the user's limb the fastener is attached to the outer surface 20 of the leg fabric.

An elongated pocket 30 is defined upon the outer surface 22 of the base portion 14 transversely disposed to the length of the legs 16 and 18. The pocket 30 is formed by a fabric strip 32 and a reinforcing strip 34 of a width and length equal to the pocket strip 32 is aligned therewith adjacent the cushioned inner surface 20. The pocket strip 32 and reinforcing strip 34 are sewn together by seams 36, FIG. 3, and the elongated pocket 30 receives a reinforcing stay 38. The stay 38 is preferably of the flattened metal coil spiral type wherein the stay is relatively flexible lengthwise to conform to the configuration of the knee when the orthosis is applied, but resists lateral deformation and the stay aids in distributing the compression forces upon the cushioned pad, as later described.

A pair of elastic straps 40 and 42 each include an inner end 44 disposed under the pocket strip 32 and sewn thereto by seams 36, and in this manner the elastic strap inner ends are affixed to the base portion 14 adjacent the outer surface 22. The strap inner ends 44 are attached to the base portion adjacent the central region of the pocket strip 32, FIG. 1, and the straps are obliquely oriented wherein the outer ends thereof extend away from each other and are oriented in a direction for attachment to the outer surface of a leg 16 or 18 as later described. The outer ends of the straps 40 and 42 are each provided with a Velcro hook fastener patch 46 sewn thereto for attaching the strap outer ends to the outer surface of the adjacent leg.

A pouch to receive the cushioned pad 48 is defined adjacent the inner surface of the base portion 14 and is formed by a fabric 50 which is affixed at three of its edges to the seam attaching the binding 24 to the base portion. The fabric 50 is folded over at 52, FIG. 3, to form a pouch 54, and the flexible nature of the pouch fabric permits the cushioned pad 48 to be readily located within the pouch as shown in FIG. 3, and retained therein by the folded edge 52.

Figure 4:
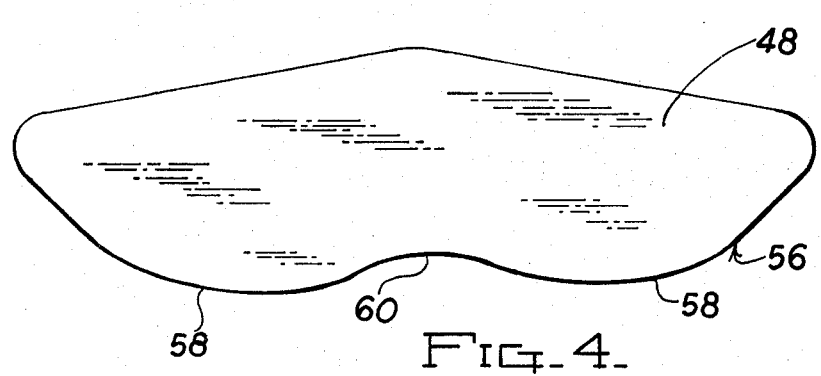
FIG. 4 is an enlarged, plan view of the cushion pad.

The cushion pad 48 is formed of a synthetic foam material of a relatively stiff consistency. As appreciated from FIG. 4, the cushion pad 48 is of a somewhat crescent configuration including a contoured side 56 including bulbous portions 58 and a recessed portion 60. The edge 62 of the base portion 14 is of a configuration complimentary to the contoured side 56 of the cushioned pad, and as will be appreciated from FIG. 2, the pad 48 is located within the pouch 54 wherein the complimentary configurations of the pad and base portion edge 62 are disposed adjacent each other. The cushioned pad is effectively maintained within the pouch 54 by the folded-over pouch portion 52, FIG. 3, and the pad may be readily removed from the pouch during washing of the orthosis, and reinstalled by manipulation of the pouch portion 52.

Figure 5:
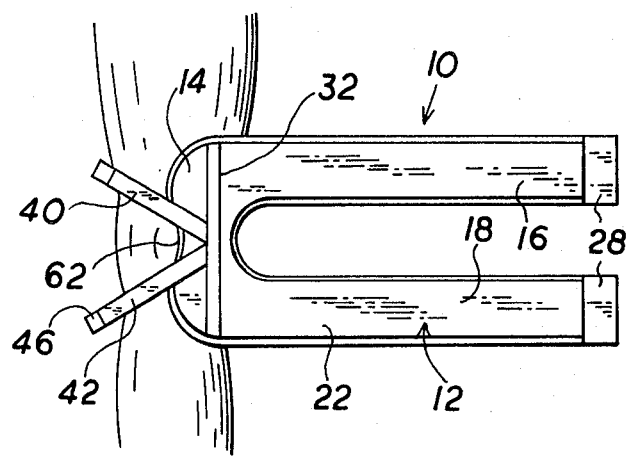
FIG. 5 is an elevational view illustrating the patellar stabilizing orthosis as initially placed upon the wearer's limb prior to wrapping.
Figure 6:
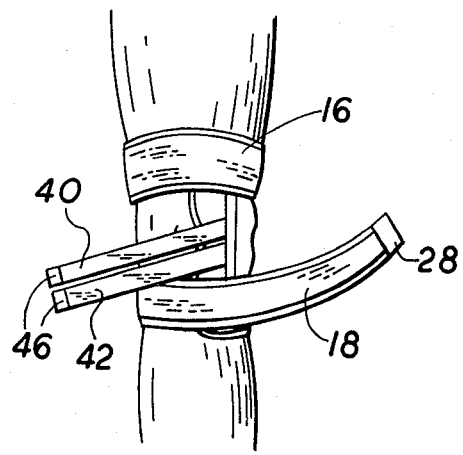
FIG. 6 is an elevational view illustrating the orthosis partially wrapped about the limb, the upper orthosis leg being wrapped, and the lower leg illustrated in a partially wrapped condition.

To apply the stabilizing orthosis of the invention to the knee, the body member 12 is initially oriented to the knee as shown in FIG. 5 wherein a left leg is illustrated having a right lateral patella instability. The inner surface 20 of the base member is disposed toward the wearer's leg, and is positioned such that pad 48 is snugly located against the side of the patella counter to the direction of the instability, the recess 60 receiving the patella central region and the pad portions 58 aiding in fitting the pad against the patella.

Upon the pad 48 and base member being properly positioned the upper orthosis leg 16 is wrapped about the wearer's thigh above the knee, and the fastener 28 of the leg 16 is fastened to the leg outer surface 22 to firmly encompass the thigh. In a like manner the lower orthosis leg 18 is wrapped about the upper portion of the calf below the knee and the fastener 28 of the lower leg 18 is attached to the associated leg outer surface 22, thereby affixing the orthosis in place upon the knee.

The upper elastic strap 40 is then pulled over the top of the patella, tensioning the strap, and the fastener 46 is attached to the outer surface 22 of the upper leg 16. The lower elastic strap 42 is then drawn downwardly and its fastener 46 is attached to the outer surface of the lower leg 18 maintaining the desired tension within the strap. The tautness or tension within the elastic straps 40 and 42 determines the extent of the traction and force against the patella, and when applying the orthosis the user adjusts the strap tension to that value which is comfortable, but which produces the desired patella stability.

The installation of the orthosis is now completed, and the orthosis may be used alone, or if other bracing appliances are employed the same may be mounted over the orthosis.

The aforedescribed orthosis is particularly effective in applying the desired pressure to the patella without producing excessive constriction of the wearer's leg. The fact that the legs 16 and 18 are nonelastic minimizes the likelihood of the legs unduly constricting the wearer's thigh and calf. However, the positioning of the elastic straps 40 and 42 is such as to produce a most effective application of force to the cushioned pad for stabilizing the patella. It is to be noted that as the base portion 14 and pad 48 are located on the same side of the patella as which the legs 16 and 18 extend from the base portion 14 that the lateral forces imposed on the pad 48 to hold the pad against the patella must be primarily created by the elastic straps 40 and 42. As the legs 16 and 18 are initially wrapped about the limb in a direction away from the patella this wrapping does not force the pad 48 in the direction of the patella and overstressing of the patella stabilization will not result from the application of the legs 16 and 18 to the limb.

The efficient distribution of patella stabilizing forces to the cushioned pad 48 arise from several factors. First, as the inner ends 44 of the elastic straps 40 and 42 are attached to the base portion outer surface adjacent the stay 38 the tension forces applied to the base portion will be distributed over the vertical height of the pad, but concentrated at the pad central region in that the strap inner ends are affixed to the base portion adjacent the central region of the stay pocket. This distribution of the forces imposed upon the pad 48 produces the inward lateral force on the pad to effectively stabilize the patella.

Figure 7:
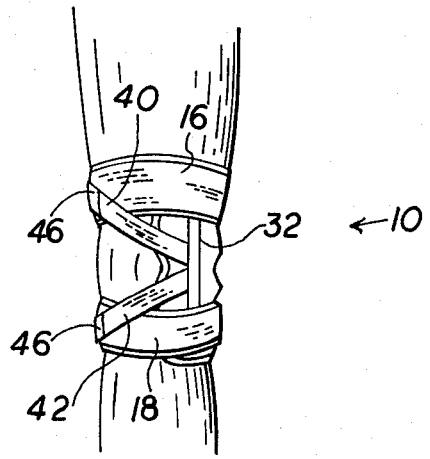
FIG. 7 is an elevational view of the orthosis as completely installed upon the wearer's knee.

A second advantage derived from the orientation of the elastic straps 40 and 42 to the base portion 14 results from the oblique orientation of the straps and the fact that the straps' inner ends are superimposed over a significant portion of the cushion pad 48. As appreciated from FIGS. 1 and 7, the inner ends of the straps extend from the stay pocket strip 32 and overlap the body base portion 14 through a considerable part of its horizontal dimension. Thus, when the straps 40 and 42 are tensioned and fastened as shown in FIG. 7 the straps produce a compression of the cushioned pad 48 which firmly maintains the pad in engagement with the limb adjacent the patella assuring the proper location of the pad with respect to the patella. However, as the straps are obliquely oriented to the body legs 16 and 18 the straps do not extend over the patella, FIG. 7, and no discomfort or compression of the patella inwardly occurs. Thus, the elastic straps are capable of producing the desired lateral force on the pad and patella to produce stabilization but the straps do not produce discomfort or forces having vectors which distract from the stabilizing effect.

As two elastic straps 40 and 42 are utilized which are symmetrically related to the base portion 14 and cushion pad 48, the straps can readily be adjusted to have equal tension therein so that a truly horizontal and symmetrical stabilizing force is imposed upon the cushion pad and patella which does not have a vertical vector, as would be the case if only a single elastic strap was employed. The extent of the lateral forces applied to the cushioned pad, and the stabilizing forces imposed upon the patella, can be very accurately controlled by adjusting the tension of the elastic straps, and their relatively short length facilitates adjustment and prevents shifting or displacement of the straps during use.

The aforedescribed patellar stabilizing orthosis eliminates posterior knee binding, as results when an elastic sleeve contains the knee, and the invention allows a free range of motion avoiding unnecessary stress to the knee joint. The adjustable tension control permitted by the straps 40 and 42 permits the pressures imposed upon the patella to be accurately adjusted for maximum efficiency and comfort, and the orthosis may be quickly applied to the wearer's leg without requiring unusual skill. Further, the construction of the orthosis reduces the need for large inventories in that only two sizes are required to fit the usual range of knee dimensions, and the orthosis may be used with either right or left limbs, without requiring modification.

The described orthosis has been found useful in rehabilitation programs involving nonsurgical patella dislocations or mal-alignments, including chondromalacia patellae, dislocation of the patella or subluxation of the patella.

It is appreciated that various modifications to the inventive concepts may be apparent to those skilled in the art without departing from the spirit and scope of the invention.

We claim:

1. A patellar stabilizing orthosis comprising, in combination, a U-shaped body formed of a nonelastic fabric having a pair of elongated substantially parallel legs interconnected by a base portion, said body having an outer surface of finely looped material and an inner surface of cushioned material, said legs each having a free end, a hooked fastener affixed to each leg free end to releasably fasten to said body outer surface, a cushioned pad mounted upon said body inner surface at said base portion, a pair of elastic straps each having an inner end affixed to said body at said base portion and a free outer end, and a hooked fastener affixed to each strap free outer end adapted to releasably fasten to said body outer surface whereby upon placing said pad laterally with respect to the patella said legs are wrapped about the wearer's leg above and below the patella and said leg free end fasteners are attached to said body outer surface and said straps extend from said base portion in the opposite direction with respect to said body legs and said strap free end fasteners are fastened to the adjacent leg outer surface placing said straps under tension.

2. In a patellar stabilizing orthosis as in claim 1, said straps' inner ends being affixed to said body base portion at said outer surface thereof.

3. In a patellar stabilizing orthosis as in claim 2, an elongated pocket defined upon said body outer surface at said base portion extending transversely to the length of said legs, a reinforcing stay within said pocket, said straps' inner ends being affixed to said body outer surface and said pocket.

4. In a patellar stabilizing orthosis as in claim 1, said body inner surface of cushioned material comprising a synthetic foam.

5. In a patellar stabilizing orthosis as in claim 3, said pocket having a central region intermediate the projection of said legs, said elastic straps' inner ends being affixed to said body and pocket at said central region and the length of said straps being obliquely oriented to the length of said legs in a direction outwardly from the center line of said body with respect to the length of said legs whereby the force produced by said straps is concentrated centrally and symmetrically with respect to said pad.

6. In a patellar stabilizing orthosis as in claim 1, a flexible pouch defined upon said body adjacent said inner surface at said base portion, said cushioned pad being removably supported within said pouch.

7. In a patellar stabilizing orthosis as in claim 6, wherein said pouch is defined by a fabric member having a folded over portion defining access to said pouch and a peripheral region sewn to the periphery of said body base portion at said inner surface.

8. In a patellar stabilizing orthosis as in claim 6, said cushioned pad being formed of a synthetic foam material of a crescent configuration and having an edge having a recessed central region disposed in a direction away from said legs and conforming to the patella.

* * * * *